US012778865B2

(12) United States Patent
Musumeci

(10) Patent No.: US 12,778,865 B2
(45) Date of Patent: Nov. 3, 2026

(54) ANHYDROUS TOPICAL DELIVERY SYSTEM FOR LIPID, AQUEOUS, AND ALCOHOL SOLUBILIZED ACTIVES

(71) Applicant: Morse Laboratories L.P., Malibu, CA (US)

(72) Inventor: Stephen Musumeci, Malibu, CA (US)

( * ) Notice: Subject to any disclaimer, the term of this patent is extended or adjusted under 35 U.S.C. 154(b) by 169 days.

(21) Appl. No.: 18/684,222

(22) PCT Filed: Aug. 18, 2022

(86) PCT No.: PCT/US2022/075116
§ 371 (c)(1),
(2) Date: Feb. 16, 2024

(87) PCT Pub. No.: WO2023/023580
PCT Pub. Date: Feb. 23, 2023

(65) Prior Publication Data

US 2024/0358610 A1 Oct. 31, 2024

Related U.S. Application Data

(60) Provisional application No. 63/234,745, filed on Aug. 19, 2021.

(51) Int. Cl.
*A61K 8/34* (2006.01)
*A61Q 19/00* (2006.01)

(52) U.S. Cl.
CPC ................ *A61K 8/34* (2013.01); *A61Q 19/00* (2013.01); *A61K 2800/591* (2013.01)

(58) Field of Classification Search
None
See application file for complete search history.

(56) References Cited

U.S. PATENT DOCUMENTS

| | | | | |
|---|---|---|---|---|
| 2016/0008263 | A1* | 1/2016 | Mendoza | A61Q 1/06 424/401 |
| 2016/0081895 | A1* | 3/2016 | Elliott | A61K 8/345 424/60 |
| 2016/0166569 | A1 | 6/2016 | Bouvier | |

FOREIGN PATENT DOCUMENTS

| | | | | | |
|---|---|---|---|---|---|
| CA | 2106566 | A1 | * | 10/1992 | |
| CN | 109260038 | A | * | 1/2019 | A61Q 5/002 |
| CN | 111329808 | A | * | 6/2020 | A61Q 19/08 |
| WO | 9218227 | A2 | | 10/1992 | |
| WO | WO-2012059158 | A1 | * | 5/2012 | A61P 27/00 |

OTHER PUBLICATIONS

Machine translation WO-2012059158-A1 (Year: 2012).*
Seeing Double_ Alban Muller Launches Moisturizing Actives _ Cosmetics & Toiletries (Year: 2017).*
Machine translation CN-109260038-A (Year: 2019).*
Machine translation CN-111329808-A (Year: 2020).*
Is a gelling agent an emulsifier—Google Search (Year: 2025).*
Extended European Search Report issued in European Patent Application No. 22859371.1, dated May 30, 2025.
International Search Report and Written Opinion issued in International Patent Application No. PCT/US22/75116, mailing date Nov. 22, 2022.
Novoseletsky, “Seeing Double: Alban Muller Launches Moisturizing Actives”, Cosmetic & Toiletries, https://www.cosmeticsandtoiletries.com/cosmetic-ingredients/natural-sustainable/news/21840908/seeing-double-alban-muller-launches-moisturizing-actives, Dec 12, 2017.

* cited by examiner

*Primary Examiner* — Robert A Wax
*Assistant Examiner* — John W Lippert, III
(74) *Attorney, Agent, or Firm* — Benesch Friedlander Coplan & Aronoff LLP

(57) ABSTRACT

A system for co-solubilizing actives in lipid, aqueous, and alcohol phases in a final uniform formulation is described. The lipid phase, aqueous phase, and alcohol phase are combined with a base formulation in a sequential specific manner to optimize the bioavailability of actives and release the actives uniformly upon application of the system to an epidermal layer of skin.

10 Claims, 1 Drawing Sheet

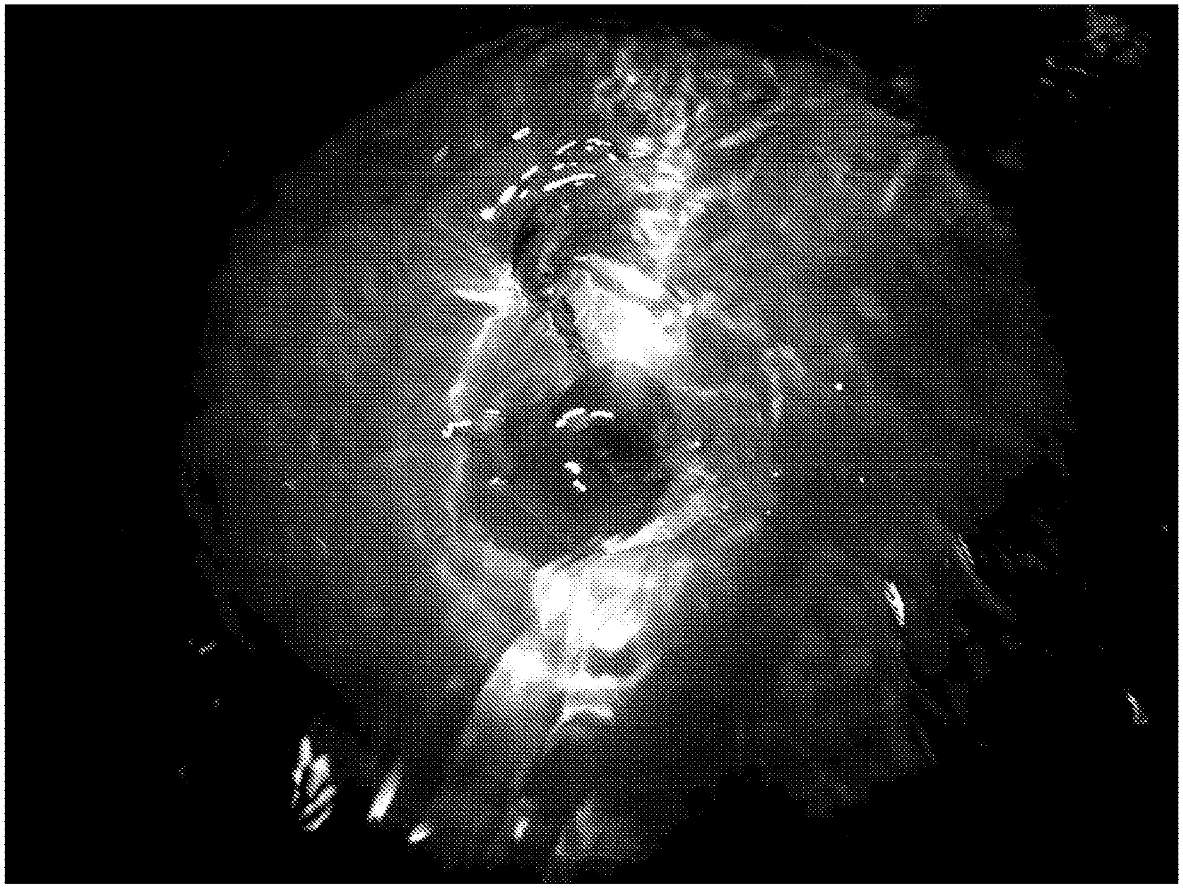

ANHYDROUS TOPICAL DELIVERY SYSTEM FOR LIPID, AQUEOUS, AND ALCOHOL SOLUBILIZED ACTIVES

CROSS-REFERENCE TO RELATED APPLICATIONS

This application claims the benefit of U.S. Provisional Application No. 63/234,745, filed Aug. 19, 2021, which application is incorporated herein by reference in its entirety.

TECHNICAL FIELD

Co-solubilized phases are combined in a specific fashion to create a delivery system where lipid, aqueous and alcohol solubilized actives to be topically applied in a single application and be readily bioavailable.

BACKGROUND

Topical Agents are used locally, where active ingredients are applied to the skin. Most common examples are creams, ointments or lotions. Most of the currently available systems have limitations because of solubility of actives or inhibition of the actives bioavailability due to the construction of the formulation.

The invention solves a long recognized problem in that art that actives that are lipid soluble, for example are not readily combinable in a single formulation with actives that are soluble in an aqueous or alcohol phase so that all actives are readily available for use in a single formulation.

SUMMARY

The invention is a system for application of a combination of active ingredients to be applied topically to a skin surface. The system including a base formulation of at least two phases and in addition a lipid phase, an aqueous phase, and an alcohol phases that are co-solubilizable with each other and with the base formulation. An active ingredient soluble in the lipid phase, the aqueous phase, or the alcohol phase is added to the base formulation. The lipid phase, aqueous phase, and alcohol phase, each with solubilized active ingredients are combined in a sequential specific manner to optimize the bioavailability of each active and release the actives uniformly upon application of the system to an epidermal layer of skin. In another aspect, the invention includes a method of applying skin beneficial agents to an epidermal layer of skin with this system.

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

BRIEF DESCRIPTION OF DRAWINGS

FIG. 1 represents an image of lipid and glycerin phases blended together at 70° C. Both phases are solubilized and remain so. The resultant solution after combinations of the phases is clear.

DETAILED DESCRIPTION

For the purposes of promoting an understanding of the principles of the present disclosure, reference will now be made to preferred aspects and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

We now describe a system for combining important actives that are oil, water and alcohol soluble into a single formulation. The system permits importantly and firstly each active to be completely solubilized and mixed uniformly in an optimal oil, water or alcohol phase optimal for that active. The phases are then combined in specific sequential steps that permit a stable final formulation to be formed. In the final formulation, each active remains in a form suitable and ready for application of the active to a surface. The contents of each phase in the final formulation link together to form a uniform phase while retaining all of the actives in a solubilized form. In this way actives that traditionally are not compatible may be co-delivered to a surface.

I. Definitions

Unless otherwise defined, all technical and scientific terms used herein have the same meaning as commonly understood by one of ordinary skill in the art to which this invention pertains. In case of conflict, the present specification, including definitions, will control.

Unless otherwise specified, "a," "an," "the," "one or more of," and "at least one" are used interchangeably. The singular forms "a", "an," and "the" are inclusive of their plural forms.

The recitations of numerical ranges by endpoints include all numbers subsumed within that range (e.g., 0.5 to 5 includes 1, 1.5, 2, 2.75, 3, 3.80, 4, 5, etc.).

The term "about," when referring to a value or to an amount of mass, weight, time, volume, concentration, or percentage is meant to encompass variations of ±1% from the specified amount. The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

Moreover, the present disclosure also contemplates that in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Summary of Invention Aspects

In one aspect, the invention is a system for application of an active ingredient to a skin surface. The system including a base formulation of at least two phases and in addition, a lipid phase, an aqueous phase, and an alcohol phases that are co-solubilizable with each other and the base formulation. An active ingredient soluble in the lipid phase, the aqueous phase, or the alcohol phase is added to that phase. The lipid phase, aqueous phase, and alcohol phase are combined in a sequential specific manner to optimize the bioavailability of the active and release the active uniformly upon application of the system to an epidermal layer of skin.

In one aspect, the system provides an active that penetrates the epidermis of the skin or remain over the skin providing a barrier. In another aspect, the active is an antiseptic, a germicide, an acne treating agent, an anesthetic, and anti-infective, and anti-rosacea agent, an antibiotic, an antifungal, an antihistamine, an antineoplastic, and anti-psoriatic, an antiviral, an astringent, a debriding agent, a depigmenting agent, an emollient, a keratolytic, an anti-inflammatory, a non-steroidal anti-inflammatory, a photochemotherapeutic, a rubefacient, a steroid or a combination of these actives.

In one aspect, a lipid phase of the system includes at least one low HLB gelling agent.

In one aspect, an alcohol phase of the system includes at least one high HLB gelling agent.

In one aspect a system in which the base formulation, a lipid phase, an aqueous phase, and an alcohol phase are first each independently formulated is followed by: combining the lipid phase and base to form a first reaction mixture, combining the aqueous phase and alcohol phase to form a second reaction mixture, combining the first and second reaction mixtures to obtain the system.

In one aspect, the system includes a base formulation including two phases—phase A and phase B. In one aspect, the system may include a phase A including safflower oil, di-alpha-tocopheryl acetate, shea butter, hydrogenated lecithin, squalene, oligopeptides, and glyceryl behenate. In one aspect, the system may include a phase B including glycerin, laureth-4, and polyethylene glyceryl behenate, and In one aspect, the system may include forming the base formulation by heating phase A and phase B, and adding phase B to phase A while mixing. In one aspect phase A and phase B are heated to 70 degrees C.

In one aspect, the system may include a lipid phase including vitamin A, a Coenzyme Q10, BVOSC, a padinami solution, a chamomile sauvage, a lavender oil, a rose oil, and a rosemary oil.

In one aspect, the system may include an aqueous lipid phase including Senestem, Bonicell, Chamomile Extract, Amiporine, Phytami White Tea, and Dismutin PF.

In one aspect, the system may include an alcohol phase including SDA 40-B, Niacinamide, and Panthenol.

In one aspect, the invention includes a method of applying skin beneficial agents to an epidermal layer of skin. The method including providing a system that has the following properties: a base formulation, a lipid phase, an aqueous phase, and an alcohol phases that are co-solubilizable with each other and the base formulation, and at least one active ingredient soluble in the lipid phase, the aqueous phase, or the alcohol phase. The method including a step of applying the system to an epidermal surface. The formulation used in the method characterized by optimized bioavailability of the active and releases the active uniformly upon the application of the system the epidermal layer of skin.

Disclosed Aspects are Non-Limiting

While various aspects of the present invention have been shown and described herein, it is emphasized that such aspects are provided by way of example only. Numerous variations, changes and substitutions may be made without departing from the invention herein in its various aspects. When any range is described herein, unless clearly stated otherwise, that range includes all values therein and all sub-ranges therein.

Characteristics of the Formulation

The system for formulating actives described herein incorporates actives that are water, oil, and alcohol soluble and incorporate them into a system where the water, alcohol, and oil soluble actives are released uniformly on the epidermal layer of the skin and remain hydrated for a prolonged period of time because they are retaining moisture under a lipid/hydroalcoholic phase. Depending on the oil being used the lipid layer can penetrate the epidermis or just remain over the skin having a hydrating barrier function.

Key ingredients of some aspects of the invention are gelling agents with emulsifying properties. Low HLB gelling agents are used in the Lipid phase. High HLB gelling agents are used in the Hydroalcoholic/alcohol phase. In some aspects, this type of system can be achieved using different types of emulsifier and gelling agents provided the low HLB emulsifiers are in the lipid phase and the high HLB emulsifiers are in the Hydroalcoholic, or alcohol, phase.

The use of HLB may be used to explained this system. Utilizing this type of explanation based on moles of ethoxylation changes the perspective and is important to this type of system. Generally a low HLB may be between about 3 and about 8, between 3 and 8, between 3 and 6, between 3.5 and 7, between 4 and 7, between 3.5 and 6 or any individual data point or range encompassed by 3 to 8. Generally a high HLB may be between about 8 and about 18, between 8 and 18, between 8 and 16, between 12 and 18, or any individual data point or range encompassed by 8 to 18. It is noted that the same effect may occur with other ingredients such soaps.

These systems of some aspects of the invention are ideal for building deliver chassis for co-delivery of lipid, aqueous, and alcohol solubilized actives.

These systems of some aspects of the invention are physically stable because they are anhydrous.

These systems of some aspects of the invention include gels are stable for a period of time greater than three years.

Besides the solubility of different actives, the inventions aesthetic characteristics, such as scent or color, can be modified by adding film formers, and different types of lipids.

The temperature both of solubilizing actives in each phase (C, D, and E) together with the temperature at which each phase (A, B, C, D, and E) is combined with each other to form a final formulation are important. Preferable the temperature is any single temperature found in the range between 50 and 80 degrees C., or between 65 and 75 degrees, or even between 68 and 72 degrees. In some cases, the phases are combined under conditions where each phase is maintained at a temperature of 70 degrees C. Further, viscosity of the system throughout the formulation process is important. Any viscosity modifier that is a type of wax and forms a linkage with similar compounds may function to maintain the viscosity of the system throughout the formulation process as described.

In some aspects, without wishing to be bound by theory, it has been found that the combination of glyceryl behenate, glyceryl behenate/eicosadioate and PEG-10 glyceryl behenate in the final formulation enhance the co-solubility, uniformity and stability of actives by linking together in the final formulation. That is, the Glyceryl Behenate/Eicosadioate may be in the oil phase and acts like a wax; Polyglyceryl-10 Behenate/Eicosadioatte may is in the Glycerin, Alcohol and Water phases and also acts like a wax. The combination of these two viscosity modifiers and Laureth 4 link and co-solubilize everything in the final formulation together. Laureth 4 has broad solubilizing properties Types of Actives Suitable Incorporation Into Any Formulation The system as described herein is not bound by the actives of the formulation. Rather, the generic system of phases A+B+C+D+E are available to any desired suitable active.

For example, the active may comprise an antiseptic or germicides that is a chemical agents that destroy microorganisms that cause disease. Topical antiseptics are applied to the skin, nails or mucus membranes to cleanse wounds and prevent infections. Antiseptic or germicides may include: chlorhexidine; povidone iodine; hexachlorophene; benzalkonium chloride; sodium hypochlorite; ethanol; silver nitrate; oxychlorosene sodium; or triclosan The active may comprise dermatological agents. The actives may include topical dermatological agents are applied directly on the skin to treat skin conditions. They may deliver medicines to prevent or treat skin disorders or have inert creams and ointments for routine skin care to maintain the skin, which may be susceptible to skin disorders. Topical dermatological agents include local anesthetics, cleansing agents, anti-inflammatory agents, anti-infective agents, emollients, astringents, agents to treat acne, anti-virals, anti-fungals, agents for psoriasis such as topical corticosteroids, and so on. The active agent may be for example topical acne agents, topical anesthetics, topical anti-infectives, topical anti-rosacea agents, topical antibiotics, topical antifungals, topical antihistamines, topical antineoplastics, topical antipsoriatics, topical antivirals, topical astringents, topical debriding agents, topical depigmenting agents, topical emollients, topical keratolytics, topical nonsteroidal anti-inflammatories, topical photochemotherapeutics, topical rubefacient, topical steroids, or topical steroids with anti-infectives.

Exemplary topical dermatological agents characterized as topical steroids with anti-infectives may include, for example, any combination of aloe vera, hydrocortisone, iodoquinol, nystatin, triamcinolone, acyclovir, fluocinolone, neomycin, ketoconazole, iodoquinol, betamethasone, clotrimazole, bacitracin, or polymyxin b.

Exemplary topical dermatological agents characterized as topical steroids may include for example any combination of mometasone, clobetasol, triamcinolone, fluocinonide, flurandrenolide, halobetasol, desoximetasone, desonide, clocortolone, hydrocortisone, betamethasone, fluticasone, fluocinolone, prednicarbate, diflorasone, halcinonide, salicylic acid, sulfur, halobetasol, methylprednisolone, amcinonide, fluticasone, or alclometasone.

Exemplary topical dermatological agents characterized as topical rubefacients may include for example any combination of methyl salicylate, camphor, menthol, trolamine salicylate, capsaicin, or eucalyptus.

Exemplary topical dermatological agents characterized as topical photochemotherapeutics may include for example any combination of methoxsalen, methyl aminolevulinate or aminolevulinic acid.

Exemplary topical dermatological agents characterized as topical non-steroidal anti-inflammatories may include for example any combination of: capsaicin, diclofenac, and menthol.

Exemplary topical dermatological agents characterized as topical keratolytics may include for example any combination of podofilox and salicylic acid.

Exemplary topical dermatological agents characterized as topical emollients may include for example any combination of ammonium lactate, urea, emollients, salicylic acid, vitamin a, d and/or e, petrolatum, lanolin, or aloe vera.

Exemplary topical dermatological is characterized as topical depigmenting agents may include for example any combination of fluocinolone, hydroquinone, tretinoin, or monobenzone.

Exemplary topical dermatological agents characterized as topical debriding agents may include for example any combination of collagenase, balsam peru, castor oil, or trypsin.

Exemplary topical dermatological agents characterized as topical astringents may include for example witch hazel.

Exemplary topical dermatological agents characterized as topical antivirals may include for example any combination of penciclovir or acyclovir.

Exemplary topical dermatological agents characterized as topical antipsoriatics may include for example any combination of: betamethasone, calcipotriene, tazarotene, halobetasol, calcitriol, anthralin, resorcinol, or methoxsalen.

Exemplary topical dermatological agents characterized as topical antineoplastics, may include for example any combination of imiquimod, ingenol, mechlorethamine, diclofenac, tirbanibulin, or fluorouracil.

Exemplary topical dermatological agents characterized as topical antihistamines may include for example any combination of diphenhydramine or doxepin.

Exemplary topical dermatological agents characterized as topical antifungals may include for example any combination of: tolnaftate, miconazole, terbinafine, undecylenic acid, ciclopirox, clotrimazole, econazole, sulconazole, salicylic acid, sodium thiosulfate, ketoconazole, butenafine, luliconazole, naftifine, nystatin, zinc oxide, sodium thiosulfate, sertaconazole, tavaborole, or efinaconazole.

Exemplary topical dermatological agents characterized as topical antibiotics may include for example any combination of: mupirocin, sulfacetamide sodium, sulfur, retapamulin, silver sulfadiazine, bacitracin, neomycin, polymyxin b, ozenoxacin, erythromycin, pramoxine, mafenide, or gentamicin.

Exemplary topical dermatological agents characterized as topical anti-rosacea agents may include for example any combination of: ivermectin, brimonidine, oxymetazoline, metronidazole, or azelaic acid.

Exemplary topical dermatological agents characterized as topical anti-infectives may include for example any combination of: docosanol, ivermectin, imiquimod, hydrogen peroxide, spinosad, permethrin, sinecatechins, benzyl alcohol, abametapir, silver, piperonyl butoxide, pyrethrins, acetic acid, boric acid, cadexomer iodine, nitrofurazone, crotamiton, chloroxine, or aloe polysaccharides/iodoquinol.

Exemplary topical dermatological agents characterized as topical anesthetics may include for example any combination of: lidocaine, pramoxine, benzocaine, dibucaine, prilocaine, zinc acetate, benzalkonium chloride, tetracaine, hydrocortisone, menthol, capsaicin, methyl salicylate, phenol, pentafluoropropane, or tetrafluoroethane.

Exemplary topical dermatological agents characterized as topical acne agents may include for example any combination of: adapalene, benzoyl peroxide, clindamycin, dapsone, tretinoin, clindamycin, azelaic acid, tazarotene, erythromycin, or sulfur.

Exemplary topical dermatological agents may include for example any combination of: pimecrolimus, tacrolimus, minoxidil, glycopyrronium, coal tar, selenium sulfide, zinc oxide, bimatoprost, diphenhydramine, sodium hyaluronate, capsaicin, salicylic acid, sulfur, pyrithione zinc, allantoin, camphor, phenol, vitamin e, balsam peru, castor oil, mequinol, tretinoin, dexpanthenol, alitretinoin, or formaldehyde.

Exemplary ingredients of phase A, a lipid-soluble heat-tolerant phase may include an acceptable oil or lipid or combination of oils. For example, safflower oil, shea butter, lecithin may serve as lipids in this formulation. Phase A may also include squalene, oligopeptides, tocopheryl acetate, a cholesterol or other sterol ester. It is appreciated however, that phase A does not necessarily include all of these ingredients. Additionally phase A may include any suitable lipid-soluble compound that is stable at temperatures up to about 70° C., e.g. phase A may contain any lipid soluble active that is heat-tolerant. Phase A additionally includes a lipid-soluble emulsifier. Preferably, the emulsifier is a glyceryl behenate/eicosadioate though any emulsifier may be used. Generally phase A is present in an amount between about 50 and 70 wt % of the final formulation, or between 50 and 70 wt %, or any individual number between 50 and 70 wt %, e.g. 52.5% for example. Preferably phase A is present in the final formulation between 53 and 66 wt %.

Exemplary ingredients of phase B, a glycerin based phase may include glycerin, and at least one emulsifier. An exemplary emulsifier may be Laurethe-4. A second exemplary emulsifier may be polyglyceryl-10 behenate/eicosadioate though any emulsifier may be used. It is appreciated however, that phase B does not necessarily include all of these ingredients. Additionally phase B may include any suitable glycerin soluble emulsifier that is stable at temperatures up to about 70° C. Generally phase A is present in an amount between about 10 and 12 wt % of the final formulation, or between 10 and 12 wt %, or any individual number between 10 and 12 wt %, e.g. 11.25 wt % for example. Preferably phase B is present in the final formulation between 11 and 12 wt %.

Exemplary ingredients of phase C, a lipid-soluble heat-sensitive phase may include any acceptable oil or lipid or combination of oils and lipid-soluble actives. Of course phase C may additionally contain lipid-soluble actives that are heat-tolerant. However, some lipid-soluble actives are in fact sensitive to the heating to 70° C. of phase A, thus it is preferable to add these heat-sensitive actives (phase C) to a mixture of phase A+B after the phase A+B mixture is cooled. Phase C may be added to the phase A+B mixture after cooling the A+B mixture to a temperature of between about ambient room temperature and 50° C., or more preferably phase C is added to the phase A+B mixture at a temperature between about 30° C. and 45° C. In addition to any lipid, Phase C may also include, for example, vitamin A, Coenzyme Q tetrehexyldecyl ascorbate, a jojoba seed oil extract, and any scents such as chamomile, lavender, rose or rosemary essential oils squalene. It is appreciated however, that phase C does not necessarily include all of these ingredients and that any additional lipid-soluble active may also be incorporated into Phase C. Generally phase C is present in an amount between about 4 and 16 wt % of the final formulation, or between 4 and 16 wt %, or any individual number between 4 and 16 wt %, e.g. 12.001% for example. Preferably phase C is present in the final formulation between 6 and 15 wt %.

Exemplary ingredients of phase D, a water-soluble phase may include any combination of water, glycerin and water-soluble actives. Phase D may also include, for example, stem cells, cell extracts, hydrolyzed algin, a laminaria digitata extract, pomegranate extract, white tea leaf extract, amiporine, appendiculata leaf extract, any enzyme or protein, such as superoxide dismuatase. It is appreciated however, that phase D does not necessarily include all of these ingredients and that any additional water-soluble active may also be incorporated into Phase D. Generally phase D is present in an amount between about 10 and 12 wt % of the final formulation, or between 10 and 12 wt %, or any individual number between 10 and 12 wt %, e.g. 11.021% etc.

Exemplary ingredients of phase E an alcohol-soluble phase may include any combination of an alcohol and alcohol-soluble actives. Phase E may also include, for example, panthenol, proline, and niacinamide. It is appreciated however, that phase E does not necessarily include all of these ingredients and that any additional alcohol-soluble active may also be incorporated into Phase E. Generally phase E is present in an amount between about 6 and 10 wt % of the final formulation, or between 6 and 10 wt %, or any individual number between 6 and 10 wt %, e.g. 9.8% for example. Preferably phase E is present in the final formulation between 7 and 9 wt %.

Surface Application

While in some aspects described herein, the system provides an optimal formulation for application to a dermatological surface, it is appreciated that the system and methods provide means for uniformly distributing co-solubilized actives to any a living or non-living surface. Such surfaces may be exemplified by for example: in conduits, tubes, etc. used in the dental office, hospital, medical facilities, household, or industry. Non-limiting examples of applications for this invention include antimicrobial products, household products and cleaners, fabric detergents, dish detergents, cleansers, soaps, bubble baths, disinfectants, deodorizers, human and animal foods, food products, beverages, preservative compositions, antimicrobial packaging, pharmaceutical products, medical devices, e.g. catheters, wound dressings, ophthalmic uses, contact lenses and storage containers, cosmetics, feminine hygiene compositions, vaginal douches, infant care products, antimicrobial soaps, hand sanitizers, deodorants, antiperspirants, anti-microbial coatings, dental compositions, toothpastes, mouth rinses and washes, oral swabs and sponges, lipsticks, dental appliances and devices, skin swabs, medications, athlete's foot treatments, cold sore treatments, herpes virus treatments, medicated chewing gums, wound care compositions, dermatological compositions, acne treatments, skin conditioners, skin moisturizers, anti-wrinkle formulations, skin whiteners sunscreens, tanning lotions, hair products, shampoos, shower gels, bubble baths, conditioners, shaving creams, spermicides.

EXAMPLES

For the purposes of promoting an understanding of the principles of the present disclosure, reference will now be made to preferred aspects and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Example 1: Process for Formula Preparation

The following phases, A-E are prepared and thoroughly mixed/solubilized prior to formula preparation. The phases are then combined with each other as described below.

TABLE 1

| Phase A: | |
|---|---|
| wt % | Ingredient Name |
| 53-66% | Oil (lipid)<br>A combination of additional lipids and lipid-soluble heat-tolerant lipid actives<br>Glyceryl Behenate (and) Glyceryl Behenate/Eicosadioate |

TABLE 2

| Phase B | |
|---|---|
| wt % | Ingredient Name |
| 11-12% | Glycerin 99.7% (Ruger)<br>Laureth - 4<br>PEG-10 Glyceryl Behenate (and) Glyceryl Behenate/Eicosadioate |

TABLE 3

| Phase C (Oil-Soluble Actives) | |
|---|---|
| wt % | Ingredient Name |
| 6-15% | A combination of lipids and lipid-soluble heat-sensitive lipid actives |

TABLE 4

| Phase D (Water-Soluble Actives) | |
|---|---|
| wt % | Ingredient Name |
| 10-12% | Any combination of water and water-soluble actives |

TABLE 5

| Phase E (Alcohol-Soluble Actives) | |
|---|---|
| wt % | Ingredient Name |
| 7-9% | Any combination of an alcohol and alcohol-soluble actives |

The sum of Phase A+B+C+D+E is 100 wt %.

Phases A+B+C+D+E are combined as follows: Weigh Phase A+B and heat each phase to 70 degrees C. Add Phase B to phase A while propeller mixing. This mixture of lipid and glycerin in the combination of A+B remains completely clear and solubilized, see FIG. 1. Cool the phase A+B (base formulation) to 35 degrees C. while sweep mixing. Add phase C to phases A+B while sweep mixing. Combine Phases D+E and mix until uniform. Add Phase D+E to phase A+B+C while sweep mixing thus providing a mixture of A+B+C+D+E that is uniform and all actives are bioavailable. Place into suitable storage container.

Example 2: Moisturizing Hand Sanitizer Formulation

A moisturizing formula that may be used, for example, as a hand treatment or sanitizer was prepared by formulating and combining the following:

TABLE 1

| Phase A: | |
|---|---|
| wt % | Ingredient Name |
| 27.400 | Safflower Oil (Arista) |
| 10.000 | dl-a- Tocopheryl Acetate (DSM) |
| 5.000 | Ultra Refined Shea Butter HMP (BioChemica/Hallstar) |
| 0.100 | Hydrogenated Lecithin |
| 19.400 | Squalane |
| 1.000 | Oligopeptides |
| 3.000 | Glyceryl Behenate (and) Glyceryl Behenate/Eicosadioate |

TABLE 2

| Phase B | |
|---|---|
| wt % | Ingredient Name |
| 9.000 | Glycerin 99.7% (Ruger) |
| 1.960 | Laureth - 4 |
| 0.500 | PEG-10 Glyceryl Behenate (and) Glyceryl Behenate/Eicosadioate |

TABLE 3

| Phase C (Oil Soluble Actives) | |
|---|---|
| wt % | Ingredient Name |
| 0.200 | Vitamin A Palmitate 1.7 MIU/g (DSM) |
| 0.500 | All-Q (Coenzyme Q10)plus (DSM) |
| 5.000 | BVOSC (Barnet Products) |
| 0.500 | Padinami (Alban Muller) |
| 0.010 | Chamomile Sauvage (Excellentia International) |
| 0.001 | Lavender Oil (Excelentia International) |
| 0.010 | Rose Oil Absolute (Excellentia International) |
| 0.001 | Rosemary Oil (Excellentia International) |

TABLE 4

| Phase D (water Soluble Actives) | |
|---|---|
| wt % | Ingredient Name |
| 2.000 | Senestem |
| 2.000 | Bonicell |
| 3.000 | Chamomile Extract (MMP) |
| 1.000 | Amiporine (Alban Muller) |
| 1.332 | Phytami White Tea (Alban Muller) |
| 0.500 | Dismutin PF (Center Chem) |

TABLE 5

| Phase E (Alcohol Soluble Actives) | |
|---|---|
| wt % | Ingredient Name |
| 3.986 | SDA 40-B |
| 1.300 | Niacinamide Powder (DSM) |
| 1.300 | Panthenol Powder (Tri K) |

The sum of Phase A+B+C+D+E is 100 wt %.

Phases A+B+C+D+E are combined as described in Example 1.

Example 3: Intensive Facial Moisturizer Formulation

The following phases, A-E are prepared and thoroughly mixed/solubilized prior to formula preparation. The phases are then combined with each other as described in Example 1.

TABLE 1

| Phase A: | |
|---|---|
| wt % | Ingredient Name |
| 9.398 | Safflower Oil-HO(Arista) |
| 10.000 | dl-a- Tocopheryl Acetate (DSM) |
| 5.000 | Ultra Refined Shea Butter HMP (BioChemica/Hallstar) |
| 13.000 | C10-30 Cholesterol Lanosterol Ester (Croda) |
| 9.610 | Squalane (Amyris) |
| 5.000 | Oligopeptide (Sederma) |
| 1.000 | Glyceryl Behenate/Eicosadioate (Ikeda) |

TABLE 2

| Phase B | |
|---|---|
| wt % | Ingredient Name |
| 9.000 | Glycerin 99.7% (Ruger) |
| 1.960 | Laureth - 4 (Croda) |
| 0.500 | Polyglyveryl-10 Behenate/Eicosadioate (Ikeda) |

TABLE 3

| Phase C (Oil Soluble Actives) | |
|---|---|
| wt % | Ingredient Name |
| 1.000 | Vitamin A Palmitate 1.7 MIU/g (DSM) |
| 3.000 | All-Q (Coenzyme Q10)plus (DSM) |
| 10.000 | Tetrahexyldecyl Ascorbate (BVOSC) (Barnet Products) |
| 1.000 | Padinami (Alban Muller) |
| 0.010 | Chamomile Sauvage (Excellentia International) |
| 0.001 | Lavender Oil (Excelentia International) |
| 0.001 | Rosemary Oil (Excellentia International) |

TABLE 4

| Phase D (water Soluble Actives) | |
|---|---|
| wt % | Ingredient Name |
| 1.000 | PhytoCellTec TM Malus Domestica (Trik Industries) |
| 1.000 | Mitosime (Barnet) |
| 1.000 | Ambiaty Extract (Bayer) |
| 1.000 | Phyko AIPF (Barnet) |
| 5.000 | Amiporine ER(Alban Muller) |
| 2.320 | Phytami White Tea (Alban Muller) |
| 0.500 | Dismutin PF (Centerchem) |

TABLE 5

| Phase E (Alcohol Soluble Actives) | |
|---|---|
| wt % | Ingredient Name |
| 6.000 | SDA 40-B (Pharmco-Aaper) |
| 1.300 | Niacinamide Powder (DSM) |
| 0.100 | L-Proline (Ajinomoto) |
| 1.300 | Panthenol Powder (Tri K) |

The sum of Phase A+B+C+D+E is 100 wt %.

One skilled in the art will readily appreciate that the present disclosure is well adapted to carry out the objects and obtain the ends and advantages mentioned, as well as those inherent therein. The present disclosure described herein are presently representative of preferred aspects, are exemplary, and are not intended as limitations on the scope of the present disclosure. Changes therein and other uses will occur to those skilled in the art which are encompassed within the spirit of the present disclosure as defined by the scope of the claims.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A system for application of an active ingredient to a skin surface, the system comprising:

a base formulation of at least two phases and in addition, a lipid actives phase, an aqueous actives phase, and an alcohol actives phases that are co-solubilizable with each other and the base formulation, at least one active ingredient soluble in the lipid actives phase, the aqueous actives phase, or the alcohol actives phase, wherein the lipid actives phase, aqueous actives phase, and alcohol actives phase are combined in a sequential specific manner to optimize the bioavailability of the active and release the active uniformly upon application of the system to an epidermal layer of skin, wherein the base formulation, having a base lipid phase and a base glycerin phase that are combined and heated to 70 degrees C.;

the lipid actives phase is added to the base formulation;

the aqueous actives phase and alcohol phase are combined with each other and then added to the base formulation/lipid phase combination, wherein the temperature of both the base formulation and lipid actives phase, aqueous actives phase, and alcohol actives phase are maintained with the range between 50 and 80 degrees, wherein the lipid actives phase, aqueous phase, and alcohol phase are solubilized with the base formulation.

2. The system of claim 1 wherein the active ingredient penetrates the epidermis of the skin or remains over the skin providing a barrier.

3. The system of claim 1 wherein the active ingredient is an antiseptic, a germicide, an acne treating agent, an anesthetic, and anti-infective, and anti-rosacea agent, an antibiotic, an antifungal, an antihistamine, an antineoplastic, and anti-psoriatic, an antiviral, an astringent, a debriding agent, a depigmenting agent, an emollient, a keratolytic, an anti-inflammatory, a non-steroidal anti-inflammatory, a photochemotherapeutic, a rubefacient, a steroid or a combination thereof.

4. The system of claim 1, wherein the lipid actives phase comprises at least one low HLB gelling agents.

5. The system of claim 1, wherein the alcohol actives phase comprises at least one high HLB gelling agent.

6. The system of claim 1, wherein the base formulation further comprises two phases, phase A and phase B, wherein phase A comprises safflower oil, di-alpha-tocopheryl acetate, shea butter, hydrogenated lecithin, squalene, oligopeptides, and glyceryl behenate, and wherein phase B comprises glycerin, laureth-4, and polyethylene glyceryl behenate, and wherein the base formulation is formed by heating phase A and phase B, and adding phase B to phase A while mixing.

7. The system of claim 1, wherein the lipid actives phase comprises a vitamin A, a Coenzyme Q10, a padinami solution, a chamomile sauvage, a lavender oil, a rose oil, and a rosemary oil.

8. The system of claim 1, wherein the aqueous actives phase comprises chamomile extract, or amiporine, Phytami White Tea, and Dismutin PF.

9. The system of claim 1, wherein the alcohol actives phase comprises niacinamide, or panthenol.

10. A method of applying skin beneficial agents to an epidermal layer of skin, the method comprising:

providing the system of claim 1, applying the system to an epidermal surface, wherein the system has the characteristic of optimized bioavailability of the active and releases the active uniformly upon the application of the system the epidermal layer of skin.

* * * * *